United States Patent
Bzdusek et al.

(10) Patent No.: US 10,124,189 B2
(45) Date of Patent: Nov. 13, 2018

(54) ISODOSE OPTIMIZATION

(71) Applicant: KONINKLIJKE PHILIPS N.V., Eindhoven (NL)

(72) Inventors: Karl Antonin Bzdusek, Madison, WI (US); Sean Frigo, Marshall, WI (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 471 days.

(21) Appl. No.: 14/783,025

(22) PCT Filed: Apr. 3, 2014

(86) PCT No.: PCT/IB2014/060391
§ 371 (c)(1),
(2) Date: Oct. 7, 2015

(87) PCT Pub. No.: WO2014/167461
PCT Pub. Date: Oct. 16, 2014

(65) Prior Publication Data
US 2016/0339268 A1  Nov. 24, 2016

Related U.S. Application Data

(60) Provisional application No. 61/810,829, filed on Apr. 11, 2013.

(51) Int. Cl.
*A61N 5/10* (2006.01)
(52) U.S. Cl.
CPC ......... *A61N 5/1031* (2013.01); *A61N 5/1047* (2013.01); *A61N 2005/1074* (2013.01)

(58) Field of Classification Search
CPC .................. A61N 5/1049; A61N 5/103; A61N 2005/1055; A61N 2005/1041
See application file for complete search history.

(56) References Cited

U.S. PATENT DOCUMENTS

| | | | |
|---|---|---|---|
| 5,027,818 A * | 7/1991 | Bova | A61N 5/10 378/65 |
| 5,373,844 A | 12/1994 | Smith et al. | |
| 6,741,674 B2 | 5/2004 | Lee | |

(Continued)

FOREIGN PATENT DOCUMENTS

| JP | 2008178619 | 8/2008 |
|---|---|---|
| WO | 2013024534 A1 | 2/2013 |

OTHER PUBLICATIONS

Kamerling, C., et al.; Isodose Curve Manipulation for Interactive Dose Shaping; 2012; 54th Annual Meeting of the American Association of Physicists in Medicine; Article No. TH-A-213AB-2; retrieved Feb. 8, 2013.

(Continued)

*Primary Examiner* — Kaylee Wilson

(57) ABSTRACT

A radiation therapy planning system (10) includes an isodose line unit (36), a region of interest unit (52), and an optimization unit (58). The isodose line unit (36) receives isodose lines planned for a volume of a subject. The region of interest unit (52) defines at least one isodose region of interest based on the received isodose lines. The optimization unit (58) generates an optimized radiation therapy plan based on the at least one defined isodose region of interest and at least one dose objective for the defined region of interest.

21 Claims, 5 Drawing Sheets

(56) References Cited

U.S. PATENT DOCUMENTS

| | | |
|---|---|---|
| 7,831,289 B2 | 11/2010 | Riker et al. |
| 2005/0111621 A1* | 5/2005 | Riker .................. A61N 5/1031 378/65 |
| 2012/0136677 A1 | 5/2012 | Ziegenhein |
| 2014/0094642 A1 | 4/2014 | Fuji et al. |

OTHER PUBLICATIONS

Photon Treatment Planning Collaborative Working Group; Three-Dimensional Display in Planning Radiation Therapy: A Clinical Perspective; 1991; Int. J. of Radiation Oncology Biol. Phys.; 21(1)79-89.

Shen, Y., et al.; The Isodose Lines Tracing Technology in the Radiation Therapy Plan System; 2011; Chinese Journal of Medical Physics; abstract.

Viana, R. S. S., et al.; Heterogeneity Correction in the Construction of Optimized Planning in Radiotherapy Using Linear Programming; 2011; Pesquisa Operacional; 31(3)565-578.

\* cited by examiner

ISODOSE OPTIMIZATION

CROSS REFERENCE TO RELATED APPLICATIONS

This application is a national filing of PCT application Serial No. PCT/IB2014/060391, filed Apr. 3, 2014, published as WO 2014/167461 A1 on Oct. 16, 2014, which claims the benefit of U.S. provisional application Ser. No. 61/810,829 filed Apr. 11, 2013, which is incorporated herein by reference.

The following relates generally to radiation therapy planning. It finds particular application in conjunction with isodose optimization in Intensity Modulated Radiation Therapy (IMRT) or in Volumetric Modulated Arc Therapy (VMAT), and will be described with particular reference thereto. However, it will be understood that it also finds application in other usage scenarios and is not necessarily limited to the aforementioned application.

A goal of radiation therapy is to deliver lethal doses of radiation to a target area or tumor while minimizing radiation to other areas especially nearby organs or organs at risk (OARs). IMRT and VMAT are specific approaches to developing radiation therapy plans that deliver radiation doses with precisely delivered beams of external radiation to a target area of a subject. IMRT is based on a point and shoot approach for one or more discrete beam angles while VMAT is based on delivery of moving beams or arcs of radiation.

An initial or ideal plan developed with IMRT includes measuring the beams of radiation at the output of a beam of radiation in a grid format (x,y) for each angle and intensity. A fluence map can be used to describe the radiation output intensity pattern delivered at each angle for each grid. Radiation beams are straight linear projections, but do include a scatter effect in a subject volume. The impact of the fluence or radiation as measured on a subject can be represented as a three dimensional dose cloud. A dose cloud is typically viewed as isodose lines superimposed on a subject image such as a X-ray Computed Tomography (CT) image. The isodose lines provide a spatial relationship between the dose and the target and/or OARs or anatomical structures visible in the image. Another technique which illustrates the impact of the fluence is a dose volume histogram (DVH) which provides a summary of 3-dimensional (3D) dose distributions in a 2-dimensional (2D) graphical format. The DVHs show the relationship between the volume of structures such as OARs and dose. Other approaches to radiation therapy are also evaluated visually with isodose lines and DVHs.

Methods exist to implement IMRT and VMAT approaches as deliverable radiation therapy plans. The methods can include fluence optimization, conversion to machine deliverable segments for use by a radiation delivery device such as a Linear Accelerator (LINAC), and in some cases optimization of the segments by a machine parameter optimizer. A LINAC produces beams of radiation which are collimated by a multi-leaf collimator (MLC). The MLC contains pieces of radiation absorbing material which are movable to block portions of the beam and therefore adjust the shape of the delivered radiation beam. An optimized plan includes instructions for segments of quantified beam quantity that is commonly referred to as Monitor Units or measured in Bq, and beam shapes determined by the shape formed by the MLC. Fluence optimization or generation of a fluence based plan typically proceeds creation of a deliverable plan. The dose cloud for a fluence based plan can differ from a dose cloud for the fluence plan converted to deliverable segments even if the segments are optimized by a machine parameter optimizer after conversion. Existing optimizers are designed to work with a set of objectives such as maximizing a dose to a tumor volume and minimizing a dose to OARs. Optimizers can construct a deliverable plan, subject to constraints, based on the objectives such as maximum/minimum dose for the tumor volume or OARs respectively and typically work directly with information from the various approaches such as IMRT. The shortcoming of this approach is that only the 2D DVH information is optimized by the machine parameter optimizer. The 3D dose cloud information is not considered by the machine parameter optimizer. In effect, two or more independent volume elements in the 3D dose cloud can map to a single objective point in the 2D DVH, and this leads to a loss of spatial specificity of 2D DVH-based objectives.

The following discloses a new and improved method for including 3D dose information in the machine parameter optimization which addresses the above referenced issues, and others.

In accordance with one aspect, a radiation therapy planning system includes an isodose line unit, a region of interest unit, and an optimization unit. The isodose line unit receives isodose lines planned for a volume of a subject. The region of interest unit defines at least one isodose region of interest based on the received isodose lines. The optimization unit generates an optimized radiation therapy plan based on the at least one defined region of interest and at least one dose objective for the defined region of interest.

In accordance with another aspect, a method of radiation therapy planning includes receiving isodose lines planned for a volume of a subject. At least one isodose region of interest is defined based on the received isodose lines. An optimized radiation therapy plan is generated based on the defined at least one isodose region of interest and at least one dose objective for the defined at least one isodose region of interest.

In accordance with another aspect, a radiation therapy planning system includes a display device, at least one input device, and one or more processors. The one or more processors are configured to receive planned isodose lines corresponding to a subject volume and visualize the planned isodose lines superimposed on an image of the subject volume on the display device. The one or more processors are further configured to receive selections of the visualized planned isodose lines from the at least one input device, define at least one isodose region of interest which includes the voxels delineated by the selected isodose lines, and calculate at least one dose objective based on the selected isodose lines. The one or more processors are further configured to generate an optimized deliverable radiation therapy plan based on the defined at least one isodose region of interest and the calculated at least one dose objective.

One advantage is that customizations based on radiation therapy plan visualizations are incorporated into an optimized radiation therapy plan.

Another advantage resides in combining visualized spatial changes and/or dose volume changes into the radiation therapy planning process.

Another advantage resides in customizing radiation therapy plans based on healthcare practitioner input or specific patient knowledge.

Another advantage resides in the dose optimization which can be delineated at the voxel level.

Another advantage resides in the creation of a deliverable plan based on either an IMRT or VMAT approach.

Still further advantages will be appreciated to those of ordinary skill in the art upon reading and understanding the following detailed description.

The invention may take form in various components and arrangements of components, and in various steps and arrangement of steps. The drawings are only for purposes of illustrating the preferred embodiments and are not to be construed as limiting the invention.

FIG. 1 schematically illustrates an embodiment of an isodose optimization system.

Figure 5:
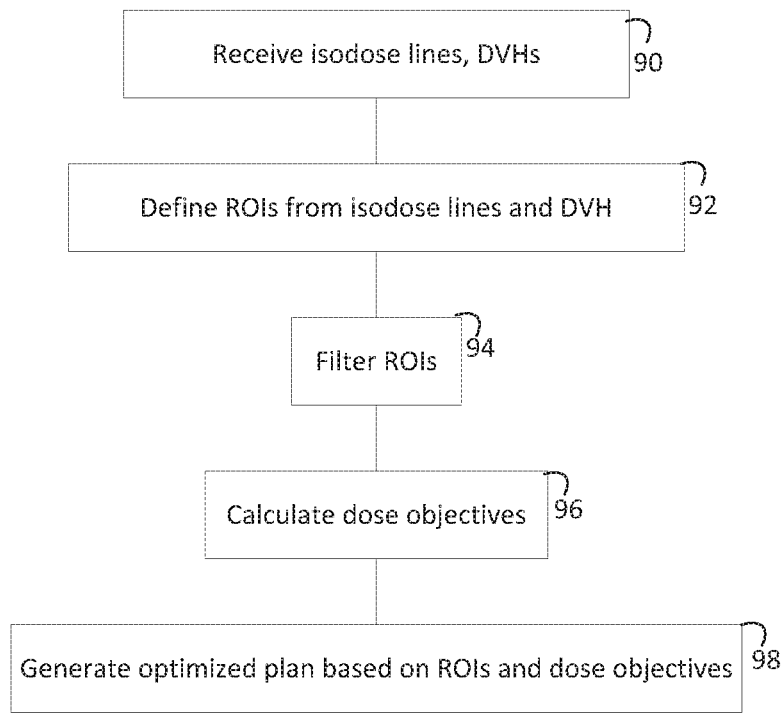

FIG. 5 flowcharts one method of isodose optimization.

Figure 1:
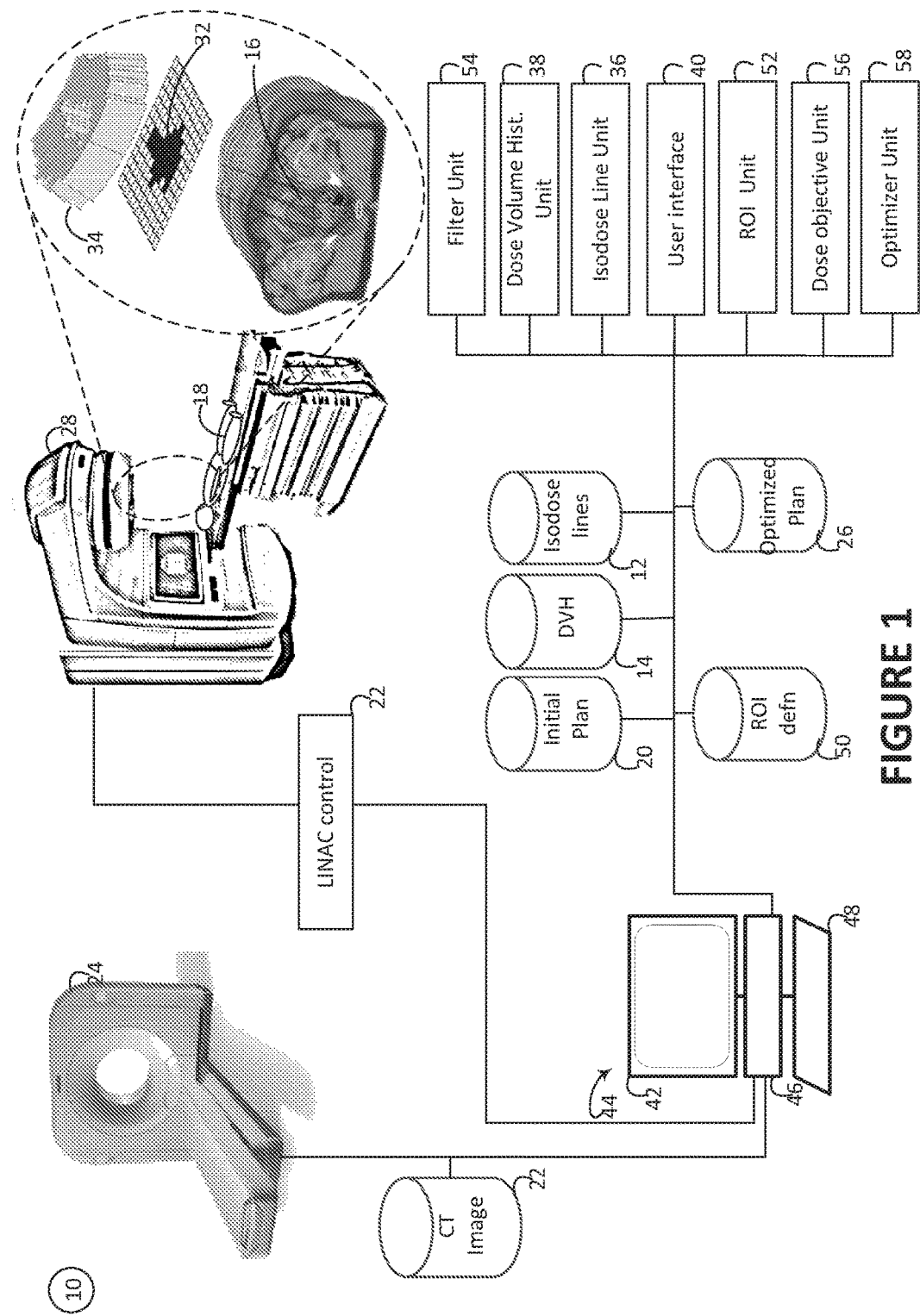

With reference to FIG. 1, an embodiment of an isodose optimization system 10 is schematically illustrated. The system can receive planned isodose lines 12 and/or dose volume histograms (DVHs) 14 for a volume 16 of a subject 18 based on an initial or ideal plan 20 based on an IMRT approach, VMAT approach, and the like, or the system can construct the isodose lines 12 and/or DVHs 14 from IMRT or VMAT information such as a dose distribution created from fluence maps. The system can receive or construct a planning image 22 such as a CT image from a CT image device 24 which corresponds to the subject volume. The optimized plan 26 includes control instructions for a radiation therapy delivery device 28 such as a LINAC. The radiation delivery device 28 includes a control 30 which executes the control instructions according to the radiation therapy plan to deliver radiation to targeted volumes of a subject. The control signals control the radiation therapy device delivery of external beams of radiation that can include a step and shoot technique or a continuous movement (dynamic) technique. The control sequences can include beam-on time, beam angle position, beam delivery rate, and instructions to shape the beam during those segments. The shape of the beam 32, represented in a 2D grid format in an exploded perspective view, is formed by movement of leaves in a multi-leaf collimator (MLC) 34 of the radiation delivery device 28 and controlled by a control 30.

The system 10 includes an isodose line unit 36 which receives or constructs isodose lines planned for the subject volume 16. The isodose lines 12 can be received in an image format, a numerical format, coordinate format, and the like. The isodose lines 12 can be constructed from a source dose grid from an approach such as fluence maps from an IMRT approach. The source dose grid can include different treatment modalities such as proton therapy or brachy therapy. The system includes a dose volume histogram (DVH) unit 38 which receives or constructs DVHs from a source dose grid planned for the subject volume 16. The isodose lines 12 and DVHs 14 can be stored in data stores. A data store can include a computer memory such as disk, flash storage, and the like and organization such as a file system, directory system, database, and the like.

The system 10 includes a user interface 40 which visualizes the constructed or received DVHs 16 and the constructed or received isodose lines 14 superimposed on the corresponding image 22. The user interface allows a healthcare practitioner to modify either of the visualized DVHs or the visualized isodose lines. A display device 42 such as a screen of a computing device 44 displays the visualized DVHs and the visualized isodose lines. The computing device 44 includes one or more electronic processors 46 and at least one input device 48 which receives the healthcare practitioner modifications to either of the visualized DVH or the visualized isodose lines. The user interface modifies the visualized DVHs according to corresponding healthcare practitioner changes to the visualized isodose lines. The user interface modifies the visualized isodose lines according to corresponding healthcare practitioner modifications to the visualized DVHs.

The computing device 44 can be a desktop computer, a laptop, a tablet, a mobile computing device, a smartphone, and the like. The input device 48 can be a keyboard, touch screen, a mouse, a microphone, and the like. The display device 42 as used herein encompasses an output device or a user interface adapted for displaying images or data. A display may output visual, audio, and or tactile data. Examples of a display include, but are not limited to: a computer monitor, a television screen, a touch screen, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), Cathode ray tube (CRT) displays, and the like.

The user interface 40 allows a user or healthcare practitioner to select isodose lines which define or delineate an isodose region of interest (ROI) 50. A ROI unit 52 defines the isodose ROI 50 based on the selected isodose lines which are stored in a data store. Each defined isodose ROI delineates a spatial volumetric area of the subject at a voxel level. A ROI can be defined as a volume of the subject selected by an isodose level, an isodose line and/or a point of a DVH curve such as a deflection point. For example, the isodose ROI can be constructed from a volume bounded by an isodose line, a volume bounded between two isodose lines, and/or a volume outside an isodose line. The selected isodose line can be selected based on the coverage or exclusion of a target area or volume of the subject. The selected isodose line can be selected based on a uniform dose, a minimum dose, or a system or user parameter.

The system 10 can include a filter unit 54 which filters the defined ROIs or a portion thereof with a surface smoothing, combining of small neighboring curves, combining neighboring portions of expansion or contraction, and the like. In one embodiment, the filtered isodose ROIs are visualized by the user interface 40 which can be reviewed by the healthcare practitioner. The filter unit 54 can include filtering based on the characteristics of the MLC 34. For example, the smoothing functions can be further weighted or modified by the leaf thickness.

The system 10 includes a dose objective unit 56 which calculates dose objectives for the defined isodose ROI. The calculated dose objective can include a function of the isodose lines which defined the isodose ROI. For example, a dose objective can include a minimum, maximum, or average of isodose levels associated with isodose lines which bound the isodose ROI. The dose objective can include a uniform value or a function of values based on the received or modified DVHs.

The system 10 includes an optimizer unit 58 which generates an optimized deliverable radiation therapy plan 20 based on the defined isodose ROIs 50 and the calculated at least one dose objective. The generated plan can include a uniform dose objective or minimum dose objective for the ROI inside a highest isodose line for the target volume. The generated plan can include a uniform dose objective, a minimum dose objective, or a minimum dose volume objective for the defined isodose ROI between a pair of lower isodose lines. The generated plan can include a maximum dose objective for the defined isodose ROI and/or defined ring shaped isodose ROI outside the target volume.

The various units or control 30, 36, 38, 40, 52, 54, 56, and 58, are suitably embodied by an electronic data processing device, such as the electronic processor or electronic processing device 46 of the computing device 44, or by a network-based server computer operatively connected with the computing device 44 by a network, or so forth. The user interface 40 includes embodiment of the computing device 44. Moreover, the disclosed visualization, ROI definition, and radiation therapy plan generation techniques are suitably implemented using a non-transitory storage medium storing instructions (e.g., software) readable by an electronic data processing device and executable by the electronic data processing device to perform the disclosed techniques.

Figure 2:
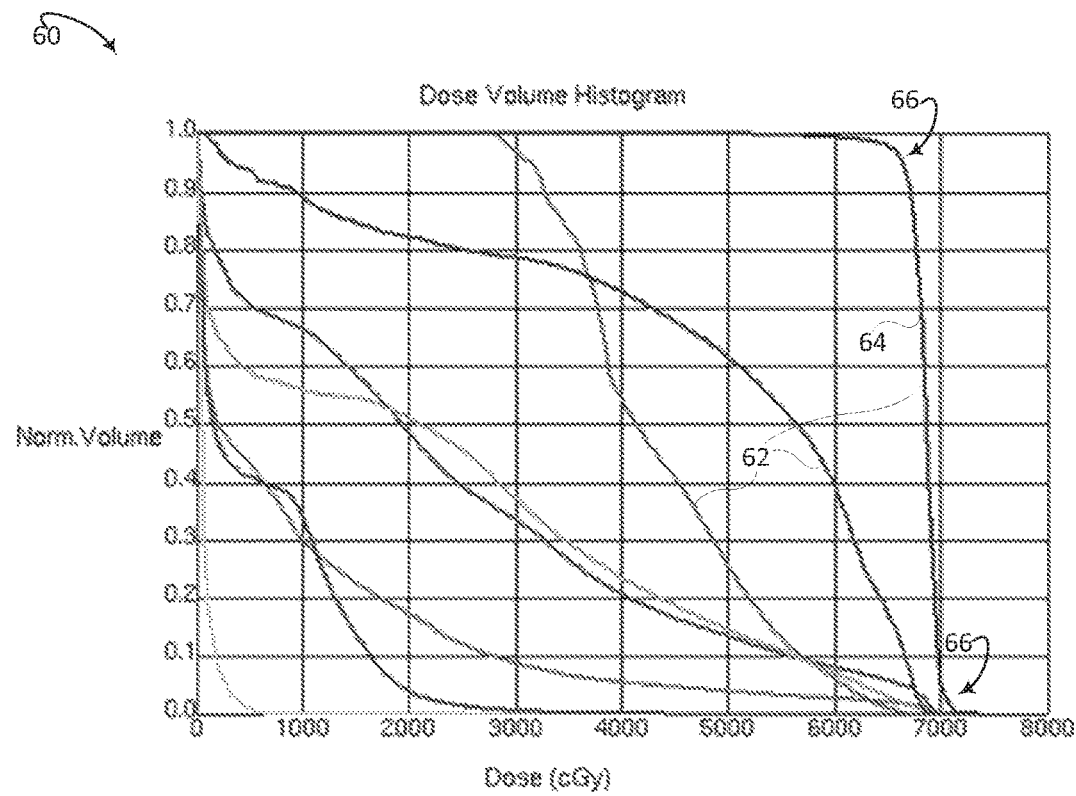
FIG. 2 illustrates a prior art exemplary visualized DVHs.

With reference to FIG. 2 an exemplary visualized integral DVHs 60 are illustrated. The DVHs can be visualized as line graphs where each line 62 represents the distribution of dose in the ROI associated with that line. Each point on the line represents dose and volume value pairs. Each point is read as the fraction of the ROI total volume receiving that amount of dose or more. The horizontal axis includes the dose in cGy. The vertical axis includes a normalized volume such as the range 0-1. The lines can include color coding or symbols, e.g. dots, hash marks, plus signs, and the like to differentiate the different intervals. For example, a line 64 shows that a nearly an entire volume such as a target volume of the subject receives a uniform dose of just under 7000 cGy. The DVH can include a legend (not shown) for the isodose lines. The user interface 40 can allow the healthcare practitioner to modify the position of the lines such as with a "drag and drop" whereby the healthcare practitioner uses an input device 48 such as a mouse to select a point on a line representation and by dragging the line modify the position of the line. The selected points can include deflection points 66 or other points. As the line changes, the other interval lines are modified accordingly. Furthermore, modifications to the DVHs 14 cause a corresponding modification to the isodose lines 12.

Figure 3:
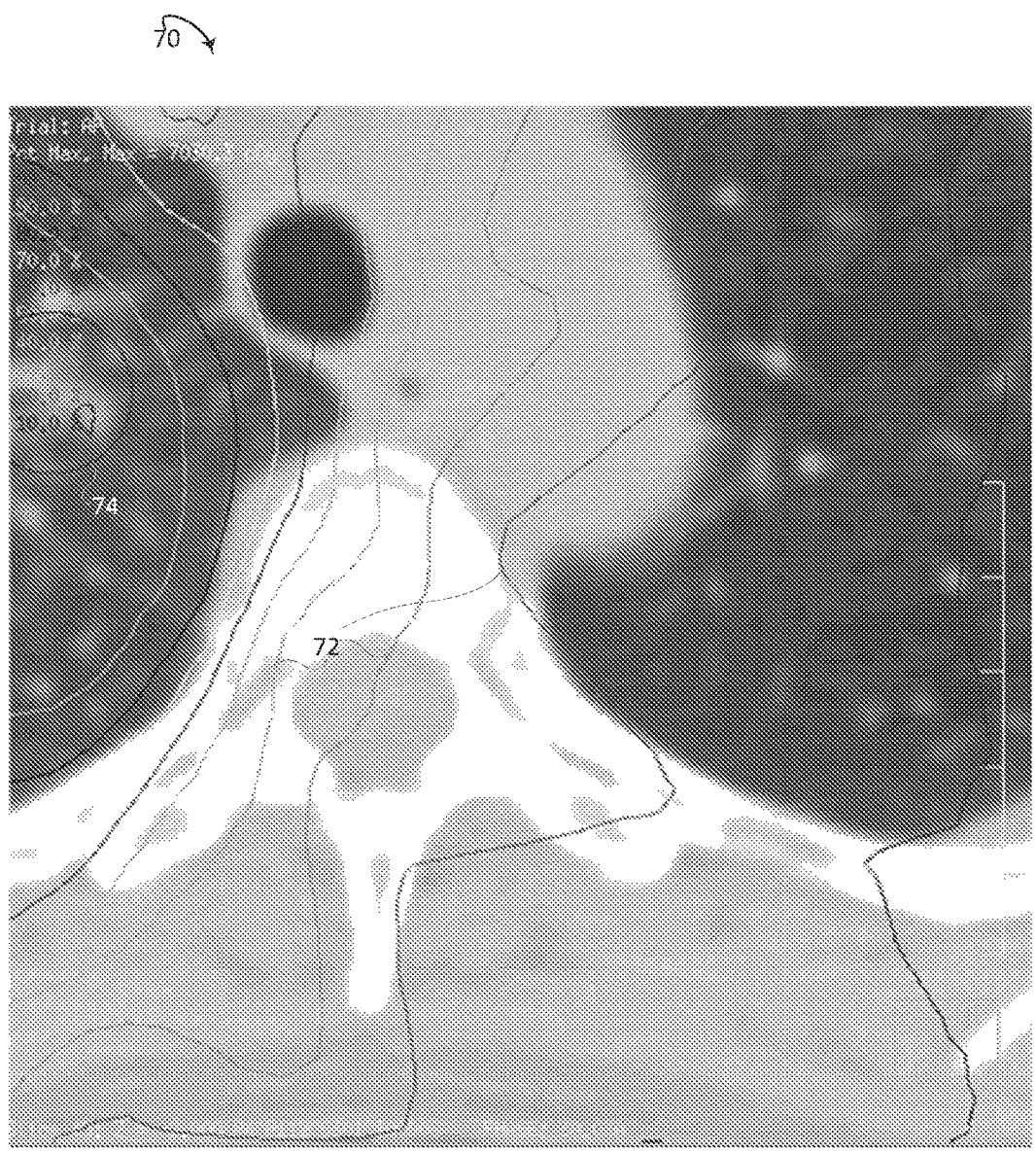
FIG. 3 illustrates a prior art exemplary visualized fluence map.

With reference to FIG. 3, exemplary visualized isodose lines are illustrated. The exemplary visualized isodose lines include an image of the subject such as a CT image with the isodose lines 72 superimposed on the image. In the image, the human vertebrae and spinal column are visible in light areas. A target volume 74 such as a tumor is located to the left side with isodose intervals lines indicated. The isodose lines are represented in color or with symbols. A legend is included in the upper left corner which indicates isodose intervals of 10%. The user interface 40 allows the healthcare practitioner to modify the position of the isodose lines with the input device 48 such as a computer mouse providing input to a software modification tool such as a paintbrush tool. The modification of the line position occurs with a "drag and drop," select and ± or zoom motion with arrow keys, movement of mouse wheel, or other like motion of an input device or combination of input devices. The user interface modifies the movement of the isodose lines corresponding to the DVH according to the modifications entered by the healthcare practitioner for the isodose lines. For example, the user can drag the isodose line that intersects the spinal column such that the entire spinal column is in the lower dose ROI.

Figure 4:
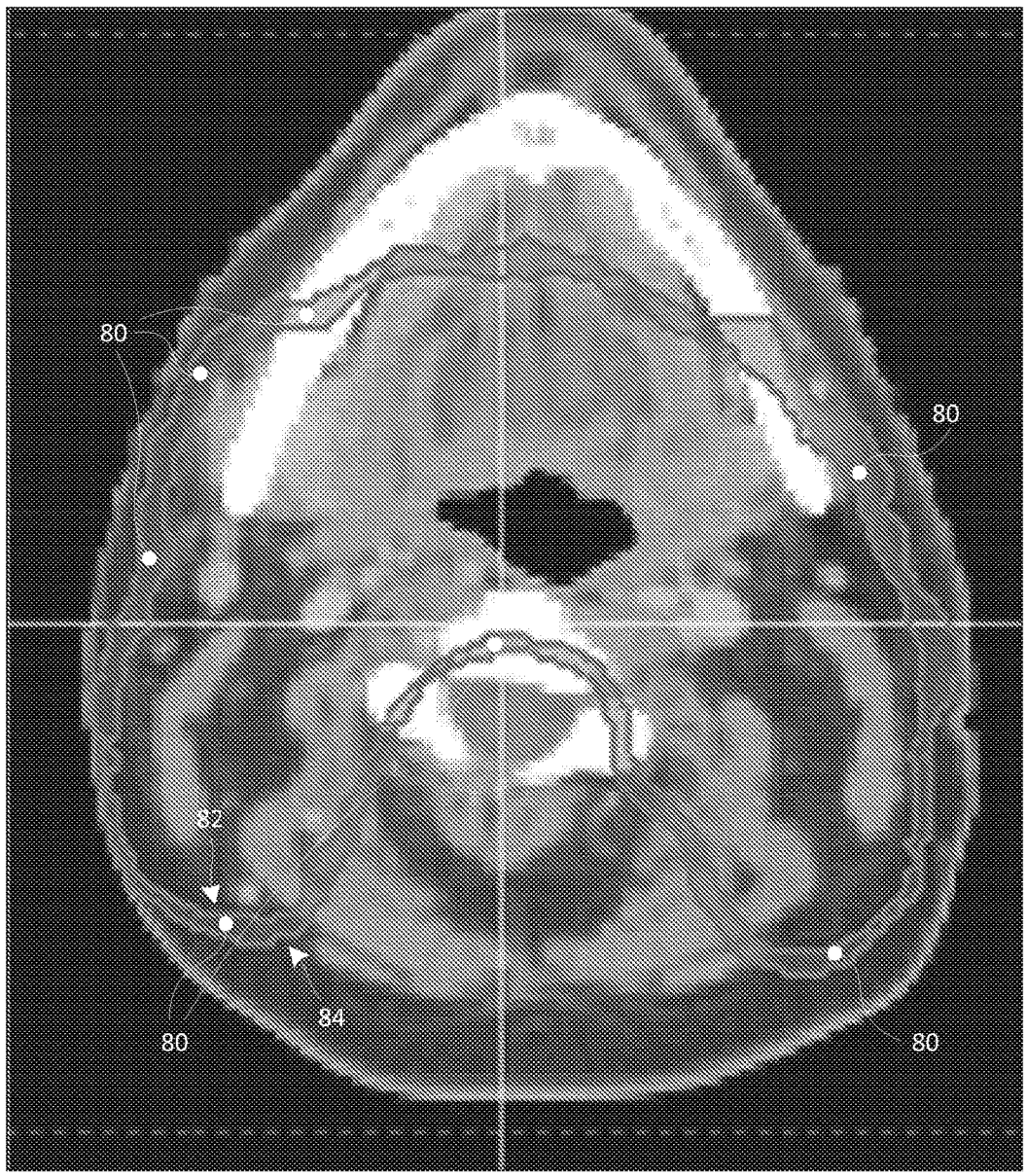
FIG. 4 illustrates an exemplary visualized isodose ROI.

FIG. 4 illustrates an exemplary visualized isodose ROI 80. The isodose ROI defines a volume at a voxel level. The defined isodose ROI 80 shown as a ring is constructed from a first volume 82 defined by a first isodose line subtracted from a second volume 82 defined by a second isodose line. The ring isodose ROI represents a volume of the subject bounded between two isodose lines. For example, a ring ROI can include the volume between two identified isodose levels such as 45 Gy to 50 Gy. The isodose ROI can be further refined by the filter unit. The ring ROI can include a uniform dose objective such as the minimum of the two identified isodose levels or 45 Gy.

FIG. 5 flowcharts one method of isodose optimization, which can be performed by one or more processors. In a step 90, isodose lines planned for a volume of a subject are received. Received isodose lines can include isodose lines 12 constructed by the isodose line unit 36 from planning approach information such as fluence maps. The step can include receiving or constructing DVHs 14 of the subject volume by the DVH unit 38. The step can include visualizing the received or constructed isodose lines superimposed on an image of the subject volume or DVHs. The step can include modification of the isodose lines and/or DVHs.

The isodose lines and/or DVHs can be modified by healthcare practitioner input through the user interface 40 such as a "drag and drop" selection and modification of isodose lines, e.g. mouse movements and/or keyboard commands. A modification to the DVHs includes a corresponding modification to the isodose lines. A modification to the isodose lines includes a corresponding modification to the DVHs. The point of selection on an isodose line, e.g. with a mouse can include a deflection point. The movement can include localized line segment manipulation parameters such as line tension, spline fitting, arc manipulation and the like which affect the degree and shape of movement and change for a dragged line. Adjusting the DVHs first is advantageous to adjust the dose in each ROI defined between adjacent isodose lines. Adjusting the isodose lines assures the various tissues have an acceptable dose level.

In a step 92, the ROI unit 52 defines isodose ROIs based on selected isodose lines. The isodose ROIs can include a volume based on a selected isodose level or interval, e.g. the region defined between a pair of adjacent isodose lines. The selected isodose level or interval can be a system supplied parameter, default system parameter, user selected parameter, and/or user default parameter. The selected isodose level can be a function of the DVH line curves. The isodose ROIs can be selected based on coverage of a target volume such as a tumor by the isodose lines and/or by voxel level changes. The selection can include input by a user or healthcare practitioner through the user interface 40. The isodose region of interest can be defined by a volume bounded by an isodose line, a volume bounded between two isodose lines, e.g. ring region, or a volume outside a volume bounded by a isodose line.

In a step 94, the defined isodose ROIs can be filtered by the filter unit 54. For example, the surfaces of the defined isodose ROIs can be smoothed, small neighboring curves combined, and/or neighboring portions of expansion or contraction combined.

In a step 96, dose objectives are added and are calculated for the defined isodose region of interest. The dose objective can include a function of isodose levels of the isodose lines used to define the isodose lines. For example, a ring shaped isodose ROI can include a minimum, maximum, or average of the isodose lines used to defined the isodose ROI. The ring shaped isodose ROI defined by a first isodose line with a level of 40 cGy and a second isodose line with a level of 45 cGy can include a dose objective calculated as min(40, 45) or 40, max(40, 45) or 45, or avg(40, 45) or 42.5, etc.

The optimization unit 58 generates a deliverable radiation therapy plan based the defined isodose ROIs in a step 98.

The generated plan can include a uniform dose objective or a minimum dose objective for the isodose ROI corresponding to a highest dose objective for a target volume. The generated plan can include a uniform dose objective, a minimum dose objective, or a minimum dose volume objective for the defined isodose ROI corresponding to a lower isodose for the target volume. The generated plan can include a maximum dose objective for a defined isodose ROI and/or defined isodose ring ROI outside the target volume. The method can include a one or more processors such as the electronic processor 46 of the computing device 44 to perform each step. The deliverable plan includes the instructions or control signals for delivery of external beams of radiation. The control signals include the amount of beam quantity such as the monitor units (MUs) or Bq's, and the control instructions to shape the MLC.

It is to be appreciated that in connection with the particular illustrative embodiments presented herein certain structural and/or function features are described as being incorporated in defined elements and/or components. However, it is contemplated that these features may, to the same or similar benefit, also likewise be incorporated in other elements and/or components where appropriate. It is also to be appreciated that different aspects of the exemplary embodiments may be selectively employed as appropriate to achieve other alternate embodiments suited for desired applications, the other alternate embodiments thereby realizing the respective advantages of the aspects incorporated therein.

It is also to be appreciated that particular elements or components described herein may have their functionality suitably implemented via hardware, software, firmware or a combination thereof. Additionally, it is to be appreciated that certain elements described herein as incorporated together may under suitable circumstances be stand-alone elements or otherwise divided. Similarly, a plurality of particular functions described as being carried out by one particular element may be carried out by a plurality of distinct elements acting independently to carry out individual functions, or certain individual functions may be split-up and carried out by a plurality of distinct elements acting in concert. Alternately, some elements or components otherwise described and/or shown herein as distinct from one another may be physically or functionally combined where appropriate.

In short, the present specification has been set forth with reference to preferred embodiments. Obviously, modifications and alterations will occur to others upon reading and understanding the present specification. It is intended that the invention be construed as including all such modifications and alterations insofar as they come within the scope of the appended claims or the equivalents thereof. That is to say, it will be appreciated that various of the above-disclosed and other features and functions, or alternatives thereof, may be desirably combined into many other different systems or applications, and also that various presently unforeseen or unanticipated alternatives, modifications, variations or improvements therein may be subsequently made by those skilled in the art which are similarly intended to be encompassed by the following claims.

What is claimed is:

1. A radiation therapy planning system, comprising:
   one or more processors configured to:
   receive or construct isodose lines from a source dose grid planned for a volume of a subject, wherein the isodose lines are representative of a shape of a radiation delivery device source beam passing through a multi-leaf collimator;
   define at least one isodose region of interest, the at least one isodose region of interest being a subset of subject voxels that are defined by-the received or constructed isodose lines; and
   generate an optimized deliverable radiation therapy plan based on the at least one isodose region of interest and at least one dose objective for the at least one isodose region of interest.

2. The system according to claim 1, wherein:
   the one or more processors are further configured to receive or construct dose volume histograms from a source dose distribution planned for the volume of the subject and
   wherein the at least one dose objective is based on the received or constructed dose volume histograms.

3. The system according to claim 2, further including:
   a user interface configured to visualize the received or constructed dose volume histograms or the received or constructed isodose lines, and to allow a healthcare practitioner to modify one of the visualized dose volume histograms or the visualized isodose lines;
   a display device configured to display the visualized dose volume histograms and the visualized isodose lines; and
   at least one input device configured to receive the healthcare practitioner modifications to one of the visualized dose volume histograms or the visualized isodose lines.

4. The system according to claim 1, wherein the at least one isodose region of interest includes
   a volume bounded between two isodose lines of the received or constructed isodose lines.

5. The system according to claim 1, wherein the at least one dose objective includes a result of a function of dose values associated with isodose lines of the received or constructed isodose lines which define the at least one isodose region of interest.

6. The system according to claim 1, wherein the at least one dose objective includes at least one of:
   at least one of a uniform dose objective or a minimum dose objective for the an isodose region of interest corresponding to a highest isodose for a target volume;
   at least one of a uniform dose objective, a minimum dose objective, or a minimum dose volume objective for an isodose region of interest corresponding to a lower isodose for the target volume; or
   a maximum dose objective for a defined at least one isodose region of interest outside the target volume.

7. The system according to claim 1, wherein:
   the one or more processors are further configured to filter at least a portion of the at least one isodose region of interest based on smoothing a surface of the region of interest.

8. The system according to claim 1, wherein the deliverable radiation therapy plan includes control signals for a radiation therapy device to deliver external beams of radiation in either one of: a step and shoot technique, or a continuous movement technique.

9. The system according to claim 8, wherein the control signals include instructions for beam quantity and MLC shapes.

10. A method of radiation therapy planning, comprising:
    receiving or constructing isodose lines from a source grid planned for a volume of a subject, wherein the isodose lines are representative of a shape of a radiation delivery device source beam passing through a multi-leaf collimator;

defining at least one isodose region of interest, the defined at least one isodose region of interest being a subset of subject voxels that are defined by the received or constructed isodose lines; and generating an optimized deliverable radiation therapy plan based on the defined at least one isodose region of interest and at least one dose objective for the defined at least one isodose region of interest.

11. The method according to claim 10, wherein receiving or constructing further includes:

receiving or constructing dose volume histograms planned for the subject; and wherein the at least one dose objective is based on the received or constructed dose volume histograms.

12. The method according to claim 10, wherein receiving or constructing includes:

visualizing the received or constructed dose volume histograms and the received or constructed isodose lines superimposed on an image of the volume of the subject; and modifying at least one of the visualized dose volume histograms or the visualized isodose lines.

13. The method according to claim 10, wherein the defined at least one isodose region of interest includes a volume outside an isodose line of the received or constructed isodose lines.

14. The method according to claim 10, wherein the at least one dose objective includes at least one of:

at least one of a uniform dose objective or a minimum dose objective for an isodose region of interest corresponding to a highest isodose for a target volume;

at least one of a uniform dose objective, a minimum dose objective, or a minimum dose volume objective for an isodose region of interest corresponding to a lower isodose for the target volume; or a maximum dose objective for a defined at least one isodose ring region of interest outside the target volume.

15. The method according to claim 10, further including:

filtering at least a portion of the defined at least one isodose region of interest based on smoothing a surface of the at least one isodose region of interest.

16. A non-transitory computer-readable storage medium carrying software which controls one or more electronic data processing devices to perform the method according to claim 10.

17. An electronic data processing device configured to perform the method according to claim 10.

18. A radiation therapy planning system, comprising:

a display device;

at least one input device; and one or more processors configured to:

receive planned isodose lines corresponding to a subject volume;

visualize the planned isodose lines superimposed on an image of the subject volume on the display device;

receive modifications of the visualized planned isodose lines from the at least one input device;

define at least one isodose region of interest which includes voxels delineated by the modified isodose lines;

calculate at least one dose objective for the defined at least one isodose region of interest; and generate an optimized deliverable radiation therapy plan based on the defined at least one isodose region of interest and the calculated at least one dose objective for the defined at least one isodose region of interest.

19. The system according to claim 18, wherein the at least one dose objective for the defined at least one isodose region of interest includes both a uniform dose objective and a minimum dose objective for an isodose region of interest corresponding to a highest isodose for a target volume.

20. The system according to claim 18, wherein the at least one dose objective for the defined at least one isodose region of interest includes both a uniform dose objective and a minimum dose volume objective for an isodose region of interest corresponding to a lower isodose for a target volume.

21. The system according to claim 18, wherein the at least one dose objective for the defined at least one isodose region of interest includes a maximum dose objective for a defined at least one isodose region of interest outside a target volume.

* * * * *